United States Patent
Engqvist et al.

(10) Patent No.: US 11,142,478 B2
(45) Date of Patent: Oct. 12, 2021

(54) TRANSLUCENT NANOCRYSTALLINE GLASS CERAMIC

(71) Applicant: ADURO MATERIAL AB, Uppsala (SE)

(72) Inventors: Håkan Engqvist, Uppsala (SE); Le Fu, Uppsala (SE); Wei Xia, Uppsala (SE)

(73) Assignee: ADURO MATERIAL AB, Uppsala (SE)

( * ) Notice: Subject to any disclaimer, the term of this patent is extended or adjusted under 35 U.S.C. 154(b) by 0 days.

(21) Appl. No.: 16/461,321

(22) PCT Filed: Nov. 16, 2017

(86) PCT No.: PCT/SE2017/051135
§ 371 (c)(1),
(2) Date: May 15, 2019

(87) PCT Pub. No.: WO2018/093322
PCT Pub. Date: May 24, 2018

(65) Prior Publication Data
US 2020/0062638 A1 Feb. 27, 2020

(30) Foreign Application Priority Data
Nov. 16, 2016 (SE) .................................. 1600326-1

(51) Int. Cl.
*C03C 10/00* (2006.01)
*A61K 6/818* (2020.01)
(Continued)

(52) U.S. Cl.
CPC .......... *C03C 10/0009* (2013.01); *A61K 6/818* (2020.01); *A61K 6/833* (2020.01);
(Continued)

(58) Field of Classification Search
CPC . C03C 10/0009; C03C 10/00; C03C 2205/06; C03C 4/0021; A61K 6/818; A61K 6/833; C03B 19/06; A61L 2430/12
See application file for complete search history.

(56) References Cited

U.S. PATENT DOCUMENTS

2014/0205972 A1  7/2014  Xia

FOREIGN PATENT DOCUMENTS

SE   WO 2014/111535 A1 * 7/2014 ............. A61K 6/027
WO      2014111535 A1    7/2014

OTHER PUBLICATIONS

Nogami, M. et al., ZrO2-Transformation-Toughened Glass-Ceramics Prepared by the Sol-Gel Process from Metal Alkoxides, J. Am. Ceram. Soc., vol. 69, No. 2, pp. 99-102 (1986).
(Continued)

*Primary Examiner* — Noah S Wiese
(74) *Attorney, Agent, or Firm* — Porter Wright Morris & Arthur LLP

(57) ABSTRACT

The present invention provides a material composition and a process of producing translucent $ZrO_2$—$SiO_2$ nanocrystalline glass ceramic (NCGC) with ultra-high flexural strength. The method comprises the following step: (1) prepare homogenous ZrO2-SiO2 nano-sized powder with high purity via a sol-gel method; (2) pressure assisted sintering of ZrO2-SiO2 nano-sized sol-gel powder to obtain translucent ZrO2-SiO2 NCGC. The invention also includes materials manufactured using the method.

27 Claims, 8 Drawing Sheets

(51) Int. Cl.
*A61K 6/833* (2020.01)
*C03C 12/00* (2006.01)
*A61C 13/083* (2006.01)
*C03B 19/06* (2006.01)

(52) U.S. Cl.
CPC ............ *C03C 12/00* (2013.01); *A61C 13/083* (2013.01); *C03B 19/06* (2013.01); *C03C 2204/00* (2013.01)

(56) References Cited

OTHER PUBLICATIONS

Official Office Action from corresponding European Application No. 17818318.2 dated Feb. 16, 2021.

\* cited by examiner

TRANSLUCENT NANOCRYSTALLINE GLASS CERAMIC

The present invention relates to a process for producing translucent $ZrO_2$—$SiO_2$ nanocrystalline glass ceramic (NCGC) with ultra-high mechanical strength by pressure-assisted sintering or pressure-less sintering. In particular, the invention provides a process for preparing $ZrO_2$—$SiO_2$ by sol-gel method and spark plasma sintering. The invention also describes materials manufactured using the method.

BACKGROUND OF THE INVENTION

Owing to their adequate mechanical properties and appealing aesthetics, ceramics and glass ceramics are widely used as dental materials. Many types of ceramics or glass ceramics have been introduced in recent years for all types of indirection restorations, from very conservative no-preparation veneers, to multi-unit posterior fixed partial dentures (FPDs) and everything between ['Ceramics in Dentistry—Part I: Classes of Materials', Inside Dentistry, 2009, Volume 7, page 94-103]. Glass ceramic developed by Ivoclar Vivadent enables to accomplish virtually all indications for all-ceramic restorations, ranging from thin veneers to 12-unit bridges [Ivoclar-Vivadent, IPS e.max Press—Scientific Documentation, 2011]. $ZrO_2$-based ceramics are definitively one of the most studied dental materials due to the fact that they possess remarkable mechanical properties, known as 'ceramic steel', and also good biological and aesthetic properties. The high strength of $ZrO_2$-based ceramics allow the realization of posterior fixed partial dentures and permits a substantial reduction in core thickness ['State of the art of zirconia for dental applications'. Dental Materials, 2008, Volume 24, page 299-307]. However, most $ZrO_2$-based all-ceramics with high bending strength are opaque and thus less aesthetically pleasing and more difficult to adapt to the colour of the surrounding teeth than glass ceramic materials. The main advantage of glass ceramics over all-ceramics in aspect of dental restoration application is their excellent translucency which offer high flexibility to adjust their shade to mimic the colour of natural human teeth, while most glass ceramic dental materials such as lithium disilicates generally have a fracture toughness and flexural strength less than half that of the all-ceramics which limits their application in dental industry. A $ZrO_2$—$SiO_2$ NCGC which combines the merits of $ZrO_2$-based ceramics and glass ceramic, namely both excellent mechanical properties and translucency, is desirable for dental restoration applications. U.S. Pat. No. 20140205972A1 provides a method of producing $ZrO_2$—$SiO_2$ glass ceramic which is characterized by hydrolyzing precursors that contains Zr and Si in solution; polymerizing of the hydrolyzed precursors in a solvent; formation of colloids comprising said polymers; formation of a gel from said colloids; aging the gel; drying the gel; and sintering the gel under formation of a glass ceramic material. The main problems with this method are that: 1) long-time drying to get a crack-free sample; 2) it is really time-consuming to obtain samples with large dimensions; (3) the mechanical strength is similar compared to present marketed glass-ceramics.

SUMMARY OF THE INVENTION

The present invention overcomes the above problems by a manufacturing method comprising synthesizing homogeneous nano-powder with high zirconia content followed by primarily pressure assisted sintering. The method comprises the following general steps:

a) Producing homogenous $ZrO_2$—$SiO_2$ nano-sized powder with high purity via a sol-gel method by using different silicon and zirconium precursors.

b) Sintering the $ZrO_2$—$SiO_2$ sol-gel powder by pressure-assisted sintering or hot isostatic pressing (HIP) or pressure less sintering with proper sintering parameters to obtain $ZrO_2$—$SiO_2$ NCGC By using the manufacturing method according to present invention it is easy to manufacture large samples. The new process can be used to produce homogenous glass-ceramic nano-sized powder with high purity even with high $ZrO_2$ content, which provides an extra degree of precipitation in a sol-gel process. By controlling the 3D crystal structure in a glass matrix, the high translucency of the material can be achieved. The pressure-assisted sintering achieves contributes to the ultra-high mechanical strength. Without wishing to be bound by any theory, controlling of the 3D crystal structure also provides rounder particles that in addition to increase the translucency, also enables better packing of the particles which improves the fracture strength. The selection of particle size probably also contributes to a better packing.

The present invention provides a process for preparing translucent $ZrO_2$—$SiO_2$ nano glass ceramic with ultra-high flexural strength. The flexural strength of the material is above 400 MPa, in some cases above 600 MPa, and for some materials even above 1000 MPa. The produced materials are still machinable by for example high speed milling.

To obtain homogenous sol-gel powder, much attention needs to be paid on the hydrolysis of the zirconium precursor.

More particularly, according to one aspect there is provided a method for preparing translucent $ZrO_2$—$SiO_2$ nanocrystalline glass ceramic, comprising the steps of:

Providing a first solution by mixing a first precursor comprising silicon (IV), a solvent and an acidic aqueous solution, whereby the first precursor is hydrolyzed;

Providing a second solution by mixing a second precursor comprising zirconium (IV) and a solvent;

Combining the first and second solutions, wherein the molar ratio between Zr and Si in said solution ranges from 20:80 to 90:10, preferably 60:40 to 80:20;

Hydrolyzing and polymerizing the combined solution by addition (preferably drop-wise) of an acidic aqueous solution to form a colloidal solution (or sol);

Ageing the sol to form a clear sol;

Polymerizing the clear sol by addition (preferably drop-wise) of an acidic aqueous solution;

Ageing the clear sol to form a gel;

Drying the gel to form a xerogel;

Micronising of the xerogel to form a powder, and optionally including particle size selection;

Calcining the powder, optionally with pre-compaction or compaction during the calcination process; and Sintering the calcined powder, optionally with pre-compaction or compaction during the calcination process.

According to another aspect, there is provided a precursor material in the form of translucent precursor glass ceramic material powder comprising 5-10 wt % of nanocrystalline tetragonal ZrO2. Said precursor material is formed after the calcination step. The precursor material may be used for dental applications such as dental restoration.

Another aspect of the present invention relates to the material produced by said method. Said material is characterized by being a translucent glass ceramic material having a microstructure of single crystalline $ZrO_2$ spherical nanocrystals embedded in an amorphous $SiO_2$ matrix, wherein the amount of $ZrO_2$ is above 30% (volume %), e.g. 35, 40, 45, 50, 55, 60, and 65 volume %. The material may be used for dental applications such as dental restoration.

According to a further aspect of the present invention, there is provided a dental restorative material comprising a translucent glass ceramic material having a microstructure of single crystalline $ZrO_2$ spherical nanocrystals embedded in an amorphous $SiO_2$ matrix, wherein the amount of $ZrO_2$ is above 30% (volume %), e.g. 35, 40, 45, 50, 55, 60, and 65 volume %.

Using the manufacturing method powder materials containing up to 65% (molar ratio) zirconia can be achieved. The molar ratio between $ZrO_2$ and $SiO_2$ of the precursor material, material, and dental restorative material ranges from 20:80 to 90:10, preferably 60:40 to 80:20. The average grain size of the sintered material is below about 400 nm.

Throughout the application, the terms "colloidal solution" and "sol" is used alternatively. The aim of the sol-gel processes is to disperse (i.e. distribute evenly) a particulate solid material in a liquid. In some stages of the processes some material may not be disbursed as the use of acid will cause salts to form and precipitate before hydrolysation causes the solid material to be dispersed. The "colloidal solution" and "sol" means a fully dispersed solid material despite that the fact that it during short periods of time may not be fully dispersed. The term "colloidal solution" is broader and encompasses sols (solution with evenly dispersed solid material), suspensions (liquid in liquid) and foams (gas in liquid), but in this disclosure we limit the term "colloidal solution" to sols.

DETAILED DESCRIPTION OF THE INVENTION

Manufacturing Method

Figure 1:
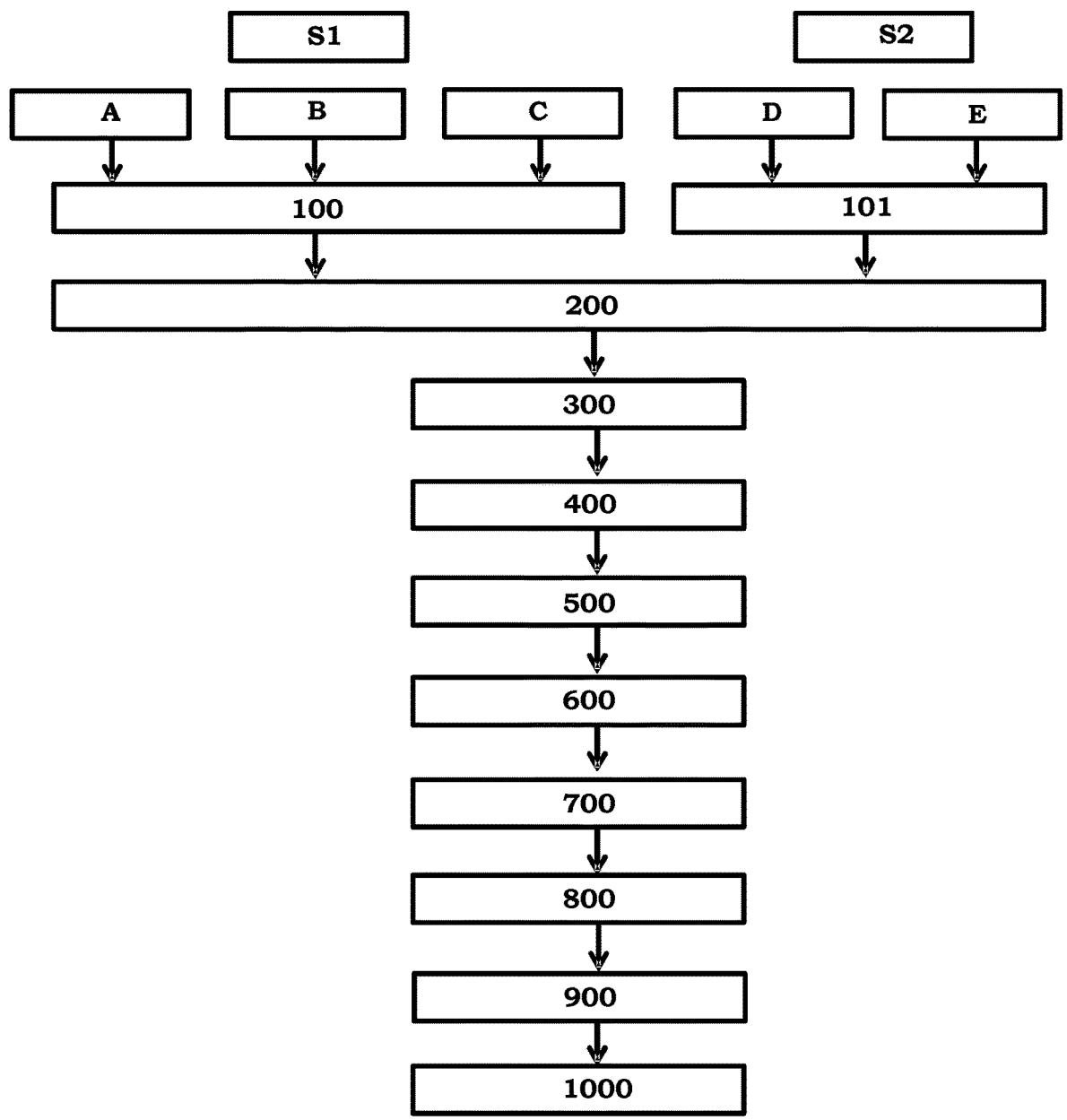
FIG. 1—Flow chart of the synthetic route followed in the $ZrO_2$—$SiO_2$ sol-gel process.

FIG. 1 shows a flow chart of the production method according to the present invention comprising steps 100-1000. Solution S1 (first precursor A comprising silicon, a solvent B, and an acidic solution C) and solution S2 (second precursor D comprising zirconium and a solvent E) are mixed and stirred separately in step 100. The acidic solution in S1 initiates the hydrolysation.

In one embodiment, the first precursor may be selected from the group consisting of tetraethyl orthosilicate (TEOS), ethyl silicate, and silicon alkoxides. In another embodiment the first precursor is selected from TEOS. In a further embodiment, the second precursor may be selected from zirconium alkoxide, such as zirconium propoxide or $Zr(OPr)_4$, zirconyl nitrate, $ZrOCl_2$ solution, and zirconium (IV)chloride. In still further embodiment the second precursor is selected from zirconium propoxide or $Zr(OPr)_4$. In yet another embodiment, the second precursor is selected from $Zr(OPr)_4$. In a still further embodiment the first and second precursors are selected from TEOS and $Zr(OPr)_4$, respectively.

In one embodiment the first precursor may suitably be diluted with anhydrous 1-propanol or anhydrous ethanol in a ratio of 1:1-1:3. In another embodiment the second precursor may be diluted with ethanol, methanol or isopropanol in a ratio of 1:0.4 to 1:3. In a further embodiment the first precursor is diluted with anhydrous ethanol in a ratio of 1:1-1:3 and the second precursor is diluted with ethanol, methanol or isopropanol in a ratio of 1:0.4 to 1:3.

The acidic aqueous solutions used in the manufacturing process may according to one embodiment be selected from a solution of HCl, $H_2SO_4$, $HNO_3$, and $CH_3COOH$, and may be used in a concentration of 0.1-12 mol/L, e.g. 0.4-12 mol/L. In another embodiment, when hydrolyzing the first precursor, the concentration may be 0.4-1 mol/L. In a further embodiment, the hydrolysation of the first precursor is performed with HCL, preferably concentrated HCL. In another embodiment, when hydrolyzing the second precursor, the concentration may be 5-12 mol/L, e.g. 7-12 mol/L. In solution 1, the ratio between acid solution (e.g. HCL) and silicon compound (e.g. TEOS) may be in the range 0.08-0.2 volume %. In the combined solution, the ratio between acid solution (e.g. HCL) and zirconium compound (e.g. zirconium propoxide) may be in the range 0.22-0.3 volume %.

In step 200, the two solutions are mixed and stirred. In step 300, an acidic solution is added (preferably drop-wise). The acidic solution initiates the final hydrolysation and polymerization until a sol is formed. In this step the second precursor is hydrolyzed using a concentration of 5-12 mol/L, e.g. 7-12 mol/L according to one embodiment. In one embodiment, the concentration of the acidic aqueous solution for the hydrolysis of the first precursor is 0.1-12 mol/L, e.g. 0.4-12 mol/L, and 5-12 mol/L, e.g. 7-12 mol/L for the hydrolysis of the second precursor.

In the mixing and acid-addition steps according to the present disclosure, the mixture was kept under vigorous stirring to avoid aggregation of white precipitates. 1 ml-3 ml acid solution was added each time with an interval of 30 min-60 min.

Step 400 involves allowing the sol to age overnight. To speed up the process, the sol may be heated above room temperature, preferably at 20-80° C., to form a clear sol.

The heating may be performed for 0.5 to 24 hours. In a further embodiment, the sol is aged for 8-12 hours at 40-80° C.

In step 500, additional acidic solution is added (preferably drop-wise). The concentration of the acidic aqueous solution may be 5-12 mol/L, e.g. 7-12 mol/L. The addition may typically be 10-20 ml.

In step 600 the sol is allowed to age to form a gel. In one embodiment, the sol may be aged for 3 hours to 3 days. In another, to speed up the process, the sol may be aged by heating it above room temperature, preferably at above 40° C., preferably at 40-80° C., more preferably at 40-70° C. In a further embodiment, the sol is aged for 2-3 days at 40-80° C.

In the subsequent step 700, the sol may be dried for 1 to 3 days to form a xerogel. In another, the sol is dried while heating at above 80° C., preferably at 80° C.-150° C. In a further embodiment, the sol is dried for 2-3 days at 80° C.-150° C.

In step 800, the xerogel is micronized by milling, such by planetary ball milling, or by grinding. The micronizing step is advantageously followed by a step of sieving the micronized material to form powders having specific particle sizes in the micrometer range. In one embodiment the particle size is 10-400 nm. In one embodiment, the powder fractions sieved in particle sizes >100 µm, 50-100 µm, and <50 µm. In another embodiment, the sieved particle size 50-100 µm is selected.

Said powder is calcined in step 900 in a furnace at above 400° C., preferably at 400-700° C. for 30-180 min, and preferably at a ramping rate of 0.5° C./min-5° C./min from room temperature to burn out the residual chemicals. In one embodiment, the furnace is Muffle furnace. In one embodiment, the powder formed after the calcination step comprises 5-10 wt % of nanocrystalline tetragonal $ZrO_2$ after calcination. The powder may be compacted with or without heating before calcination (pre-compaction) or be compacted during calcination.

In the final step 1000, the calcined powder is sintered. In one embodiment, the pressure of the sintering chamber was evacuated to lower than about 10 Pa at the beginning of the sintering. The powder may be compacted with or without heating before sintering (pre-compaction) or be compacted during sintering. In one embodiment, the sintering is performed by spark plasma. In another embodiment, the sintering is performed by spark plasma at temperatures of 900-1250° C. for 4-12 minutes. According to another embodiment, the sintering is performed by hot isostatic pressing (HIP)/or hot pressing. In another embodiment, the sintering is performed by hot isostatic pressing at temperatures of 900-1400 for 30-300 minutes. An exemplary procedure could be as follows. When pressure is applied, e.g. by punch, a uniaxial pressure may be applied gradually at the punch unit, reaching a maximum of 40 MPa-100 MPa before the temperature reaches 600° C.-900° C. and the pressures may be maintained during the whole sintering process. In another embodiment, a two-step heating process may be applied with a ramping rate of 80-150° C./min from 366° C. to 700° C.-1000° C., and 20-50° C./min from 700° C.-1000° C. to holding temperature. The holding temperature could be above 1000° C. The dwelling time may be above about 2 min.

According to one embodiment, the molar ratio between $ZrO_2$ and $SiO_2$ ranges from 20:80 to 90:10, preferably 60:40 to 80:20 in the final material.

The resulting material is a $ZrO_2$—$SiO_2$ nano glass ceramic where the spherical tetragonal $ZrO_2$ nanocrystals feature a crystal size ranging from 10 to 400 nm, such as 10 to 60 nm or 50-100 nm. The $ZrO_2$ particles are embedded in an amorphous $SiO_2$ matrix.

In an exemplary embodiment, solution S1 is prepared by mixing and stirring tetraethyl orthosilicate (TEOS), ethanol, and HCl solution (0.4 mol/L). Solution S2 is prepared by mixing and stirring $Zr(OPr)_4$ and anhydrous 1-propanol. The two solutions are combined and stirred. 15 ml HCl solution (12 mol/L) is added (preferably drop-wise) to the mixture and the formed sol is put into an oven where it was kept at 60° C. overnight to produce a clear sol. Subsequently, 10-20 ml HCl solution (12 mol/L) was added (preferably drop-wise) and then the sol was again put in the oven and kept at 60° C. for 3 days for aging and gelation. The temperature of the oven was raised to gel 120° C. to allow the gel to dry for another three days to form a xerogel. The xerogel was milled and sieved to form a translucent $ZrO_2$—$SiO_2$ nanocrystalline glass ceramic powder.

A Translucent Precursor Glass Ceramic Material

According to another aspect, there is provided a precursor material, a translucent glass ceramic material powder comprising 5-10 wt % of nanocrystalline tetragonal $ZrO_2$. Said precursor is formed after the calcination step. The molar ratio between $ZrO_2$ and $SiO_2$ may range from 20:80 to 90:10, preferably 60:40 to 80:20. The amount of $ZrO_2$ is above 30% (volume %). The crystal size of the $ZrO_2$ spherical nanocrystals ranges from 10 nm to 50 nm.

A Translucent Glass Ceramic Material

According to one aspect of the invention, there is provided a translucent glass ceramic material having a microstructure of single crystalline $ZrO_2$ spherical nanocrystals embedded in an amorphous $SiO_2$ matrix, wherein the amount of $ZrO_2$ is above 30% (volume %), e.g. 35, 40, 45, 50, 55, 60, and 65 volume %.

In one embodiment, the crystal size of the $ZrO_2$ spherical nanocrystals ranges from 10 nm to 400 nm. The molar ratio between $ZrO_2$ and $SiO_2$ may range from 20:80 to 90:10, preferably 60:40 to 80:20. In another embodiment, the only crystalline phase in the material is tetragonal $ZrO_2$. In a further embodiment, at least 99% of the material is fully densified. The material exhibits a flexural strength above 400 MPa, above 500 MPa, 600 MPa, above 700 MPa, above 800 MPa above 900 MPa, and above 1000 MPa. In one embodiment, the fracture toughness is above about 2 MPa $\sqrt{m}$.

Dental Restorative Material

According to a further aspect of the present invention, there is provided a dental restorative material comprising a translucent glass ceramic material having a microstructure of single crystalline $ZrO_2$ spherical nanocrystals embedded in an amorphous $SiO_2$ matrix, wherein the amount of $ZrO_2$ is above 30% (volume %), e.g. 35, 40, 45, 50, 55, 60, and 65 volume %.

In one embodiment, the crystal size of the $ZrO_2$ spherical nanocrystals ranges from 10 nm to 400 nm. The molar ratio between $ZrO_2$ and $SiO_2$ may range from 20:80 to 90:10, preferably 60:40 to 80:20. In another embodiment, the only crystalline phase in the material is tetragonal $ZrO_2$. In another embodiment, the only crystalline phase in the material is tetragonal $ZrO_2$. In a further embodiment, at least 99% of the material is fully densified. The material exhibits a flexural strength above 400 MPa, above 500 MPa, 600 MPa, above 700 MPa, above 800 MPa above 900 MPa, and above 1000 MPa. In one embodiment, the fracture toughness is above about 2 MPa$\sqrt{m}$.

EXAMPLES

Example 1

Preparation of $ZrO_2$—$SiO_2$ Sol-Gel Powder

Sol-gel powders of three compositions in the $xZrO_2\cdot(100-x)SiO_2$ system were fabricated (x=45, 55, 65 mol %).

In this study, specimens were designated as 45Zr, 55Zr and 65Zr, respectively. The sol-gel procedure is shown in FIG. 1. The chemicals used in the sol-gel procedure are shown in Table. 1. Tetraethyl orthosilicate (TEOS) (Sigma-Aldrich, St Louis, Mo., USA) and zirconium propoxide or $Zr(OPr)_4$ (70 wt % in 1-propanol from Sigma-Aldrich) were used as the starting alkoxide precursors. To prepare solution 1, ethanol (EtOH, >99%), HCl (aq, 0.4 mol/L) and TEOS were mixed in a 500 mL round bottom flask and was magnetic stirred for two hours. We noticed the strong reactivity of $Zr(OPr)_4$ with water. Hence, $Zr(OPr)_4$ was diluted with anhydrous 1-propanol (99.7%, Sigma-Aldrich) with a ratio of 1:1. To prepare solution 2, $Zr(OPr)_4$ and anhydrous 1-propanol were mixed in a 250 mL round bottom flask and kept stirring for two hours. Stratification can be observed in the first 20 min, then $Zr(OPr)_4$ was fully dissolved in 1-propanol to form homogenous solution. Solution 2 in the 250 mL flask was transferred to solution 1 in the 500 mL flask, followed by stirring for another two hours.

It has been found that the preparation of homogenous sol-gel powder is the key point of obtaining good glass ceramic sample before SPS sintering. To obtain homogenous sol-gel powder, much attention has been paid to the hydrolysis of $Zr(OPr)_4$. The addition of HCl solution implies the addition of water and the consequence is initiation of the final hydrolysis and polymerization of the sol. Fuming HCl solution from Acros organics (37 wt %, pure, fuming, Acros organics, Fisher Scientific) was added drop by drop using mL pipette. White precipitates appeared as soon as one drop of HCl solution was added in the sol. To avoid aggregation of white precipitates, the mixture was kept under strong stirring and 1 mL HCl solution was added each time with an interval of 30 min. The sol was moved to an oven after the addition of 15 mL HCl solution and kept at 60° C. overnight to further dissolve the white precipitates. Further HCl solution was added using the same way. Then, the sol was put into an oven (60° C.) for three days for gelation and aging. It took approximately 8 h for the sol to become gel. A drying process was carried out by transferring the gel to a beaker and raising the temperature to 120° C. for another three days. The xerogel was milled by planetary ball milling, using $ZrO_2$ milling jar and balls. The powder was then sieved to three size ranges: >100 μm, 50-100 μm, and <50 μm. Powder with particle size of 50-100 μm was used for SPS. Pre-calcination of the sieved powder was carried out in a Maffle furnace at 600° C. for 1h with a ramping rate of 1° C./min from room temperature to burn out the residual chemicals.

TABLE 1

Chemicals used in the preparation of $ZrO_2$—$SiO_2$ sol-gel powder

| Composition (mol %) | Solution 1 (mL) | | HCl (0.4 mol/L) | Solution 2 (mL) | | HCl (12 mol/L) |
|---|---|---|---|---|---|---|
| | TEOS | EtOH | | $Zr(OPr)_4$ | 1-propanol | |
| 45$ZrO_2$—55$SiO_2$ (45Zr) | 85.8 | 22.4 | 6.9 | 140.9 | 140 | 30.5 |
| 55$ZrO_2$—45$SiO_2$ (55Zr) | 64.3 | 16.8 | 5.2 | 157.8 | 200 | 34.0 |
| 65$ZrO_2$—35$SiO_2$ (65Zr) | 54.0 | 14.1 | 4.3 | 200.0 | 250 | 43.6 |

Example 2

Spark Plasma Sintering to obtain $ZrO_2$—$SiO_2$ Glass Ceramic

The pre-calcined sol-gel powders were sintered by means of spark plasma sintering (SPS-825, Fuji Electronic Industrial Co., Ltd, Japan). About 3.3 g of the powders were loaded in a graphite die (20 mm diameter) and two punch units. A low pressure (approximately 10 Pa) was applied to the die before loading it to SPS machine. The pressure of the chamber was evacuated to lower than 10 Pa at the beginning of the sintering experiment. A uniaxial pressure was applied gradually at the punch unit, reaching a maximum of 60 MPa before the temperature reaches 800° C. and maintains the pressure during the whole sintering process. The instrument took 1 min to warm up from room temperature to 366° C. After that, a two-step heating process was applied: 120° C./min from 366° C. to 900° C., and 30° C./min from 900° C. to 1150° C. The temperature was monitored by an optical pyrometer focused on a non-through hole of the graphite die. The dwelling time was 5 min.

To remove graphite sheet warped on the sintered specimen disks (around 20 mm in diameter and 2.5 mm in thickness), samples were wet grounded step-by-step by using an automatic polishing machine and 120[#], 320[#], 500[#], 800[#], 1200[#] grit papers, followed by step-by-step fine polishing process using 6 μm, 3 μm, diamond paste. The surface roughness values of the specimens were in nanometer scale (as shown in Table. 2), indicating that the negative effects of pores and micro cracks on sample surface were minimized during mechanical testes.

TABLE 2

Apparent density, relative density, grain size, surface roughness and crack length of SPSed glass ceramics.

| Material | Apparent density (g/cm$^3$) | Relative density (%) | Crystal size of ZrO$_2$ (nm) | Roughness Ra (nm) | Crack length$^a$ (μm) |
|---|---|---|---|---|---|
| 45Zr | 3.82 ± 0.01 | 99.1 | 29.5 ± 4.6 | 15.9 ± 1.2 | 39.9 ± 0.8 |
| 55Zr | 4.14 ± 0.02 | 98.8 | 35.1 ± 5.4 | 28.1 ± 8.6 | 26.1 ± 3.3 |
| 65Zr | 4.53 ± 0.03 | 99.8 | 47.5 ± 5.7 | 27.9 ± 4.8 | 18.8 ± 1.9 |

$^a$The length of cracks emanating from the corners of the square Vickers diamond impression.

Mechanical Test for the ZrO$_2$—SiO$_2$ Glass Ceramic

Piston-on-three-ball test was selected to evaluate the flexural strength of at least 4 specimens from groups 1, 2, and 3 in this study. The polished specimens were supported on 3 symmetrically spaced balls with a 3.445 mm support circle radius. Loading rate at 1 mm/min was applied by use of a universal testing machine (Autograph AGS-H; Shimadzu, Japan) with a steel rod at the center of the specimens until fracture occurred. Poisson's ratio was set as 0.3 in this experiment. The maximum load was recorded and the biaxial flexural strength was calculated according to the equation suggested by the test standard (ASTM F 394-78) as follows:

$$S = -0.2387 P(X-Y)/d^2 \quad (2)$$

Where S is the maximum tensile stress (MPa), P is the load at fracture (N), and d is the specimen thickness at fracture origin (mm). X and Y are determined as follows:

$$X = (1+\gamma)\ln\left(\frac{B}{C}\right)^2 + [(1-\gamma)/2]\left(\frac{B}{C}\right)^2 \quad (3)$$

$$Y = (1+\gamma)\left[1 + \ln\left(\frac{A}{C}\right)^2\right] + (1-\gamma)(A/C)^2 \quad (4)$$

Where γ is the Poisson's ratio, B is the radius of the tip of the piston (0.8 mm), and C is the radius of the specimen.

The Vickers hardness was determined by a micro hardness tester (Buehler Micromet 2104, Lake Bluff, Ill., USA)) with an indentation load of 2 kgf. Crack length and indentation diagonals were immediately measured by using the equipped software on the device. At least 12 indentations on each sample were done. Optical micrographs of indention were obtained by an Olympus AX70 light microscope (Olympus Corp., Tokyo, Japan).

A nano indentation tester (Ultranano-indenter, CSM instruments) was used to measure the Young's modulus and hardness on the nanoscale with a load of 8000 μN at a speed of 8000 μN/min. 12 indentations with proper distance from each other were done for each sample. Young's modulus was calculated according to Oliver-Pharr method. The equation is $$E = \frac{1-\gamma^2}{(2\beta - S_u)\sqrt{A/\pi} - (1-\gamma_i^2)/E_i} \quad (5)$$

where γ is Poisson's ratio of specimens, β is Oliver-Pharr constant, $S_u$ is slope at start of unloading curve, A is indenter area function, $\gamma_i$, $E_i$ are Poisson's ratio and Young's modulus of indenter material, respectively.

The equation proposed by Niihara K for Palmqvist cracks (1/a<2.5) was used to calculate the fracture toughness:

$$K_c = 0.018 H_v \sqrt{a} \left(\frac{E}{H_v}\right)^{2/5} \left(\frac{l}{a}\right)^{-1/2} \quad (6)$$

where α is the indentation diagonal, E is the Young's modulus, $H_v$ is the Vickers hardness and l is the crack length from the indent tip. Young's modulus and Vickers hardness were obtained from nano indentation and micro indentation, respectively.

Phase Identification and Microstructure Characterization

Both sol-gel powders and SPSed specimens were subjected to X-ray diffraction measurement (Diffractometer D5000, Siemens, Germany). XRD patterns were recorded in the range of 5° to 80° with a scan step of 0.2 s/step and a step size of 0.02° by use of Ni filtered Cu Kα X-ray resource.

Scanning electron microscopy (SEM, Merlin, Zeiss, Germany) was used to characterize the morphology of the powders and sintered glass ceramics. Polished sample surfaces of glass ceramics were etched for 1 h with HF gel. Fracture surfaces were also subjected to SEM observation after piston-on-three-ball tests. Higher resolution studies were performed on a Titan 80-300 transmission electron microscope (TEM, FEI Company, The Netherlands) operated at 300 kV. Images were recorded in bright-field TEM, high-resolution TEM (HRTEM), and high-angle annular dark-field STEM (HAADF STEM), which shows compositional contrast. Complementary selected area electron diffraction (SAED) patterns were recorded to determine crystallinity. Elemental information was obtained from Electron Energy Loss Spectroscopy (EELS) on a Quantum GIF (Gatan Inc., Pleasanton, Calif.).

Characterization of Sol-Gel Powder

Figure 2:
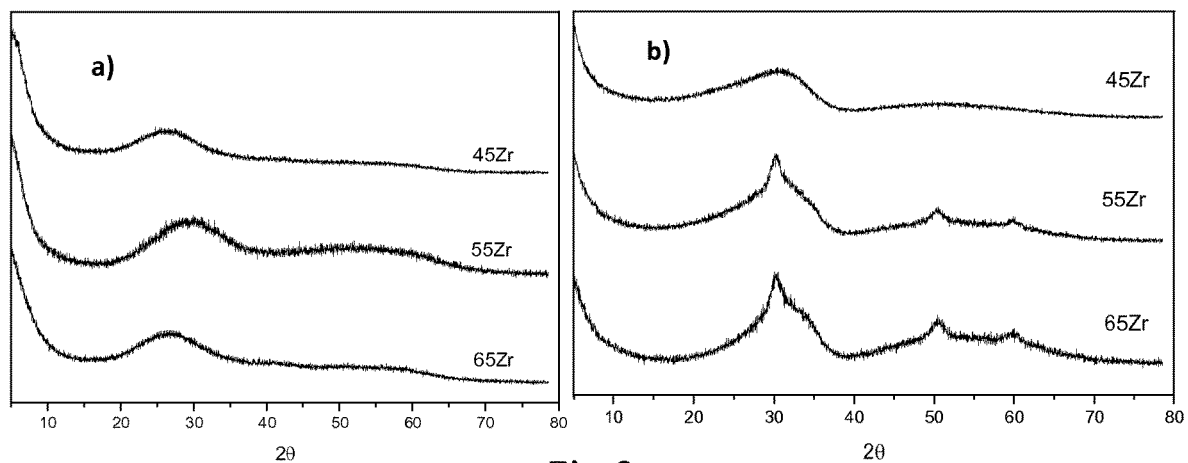
FIG. 2—XRD patterns of sol-gel powders: (a) before calcination; (b) after calcination at 600° C. for 1h, with a ramp rate of 1° C./min.
Figure 3:
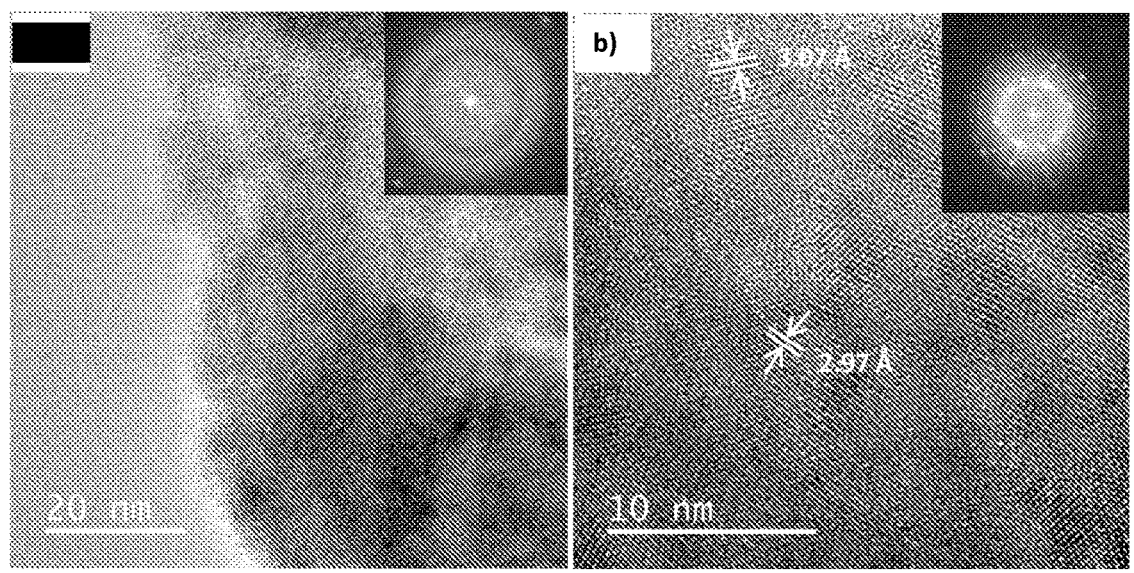
FIG. 3—HRTEM images of 65Zr sol-gel powder after calcination: a) amorphous region; b) nano-sized $ZrO_2$ region, FFT pattern is inserted.
Figure 4:
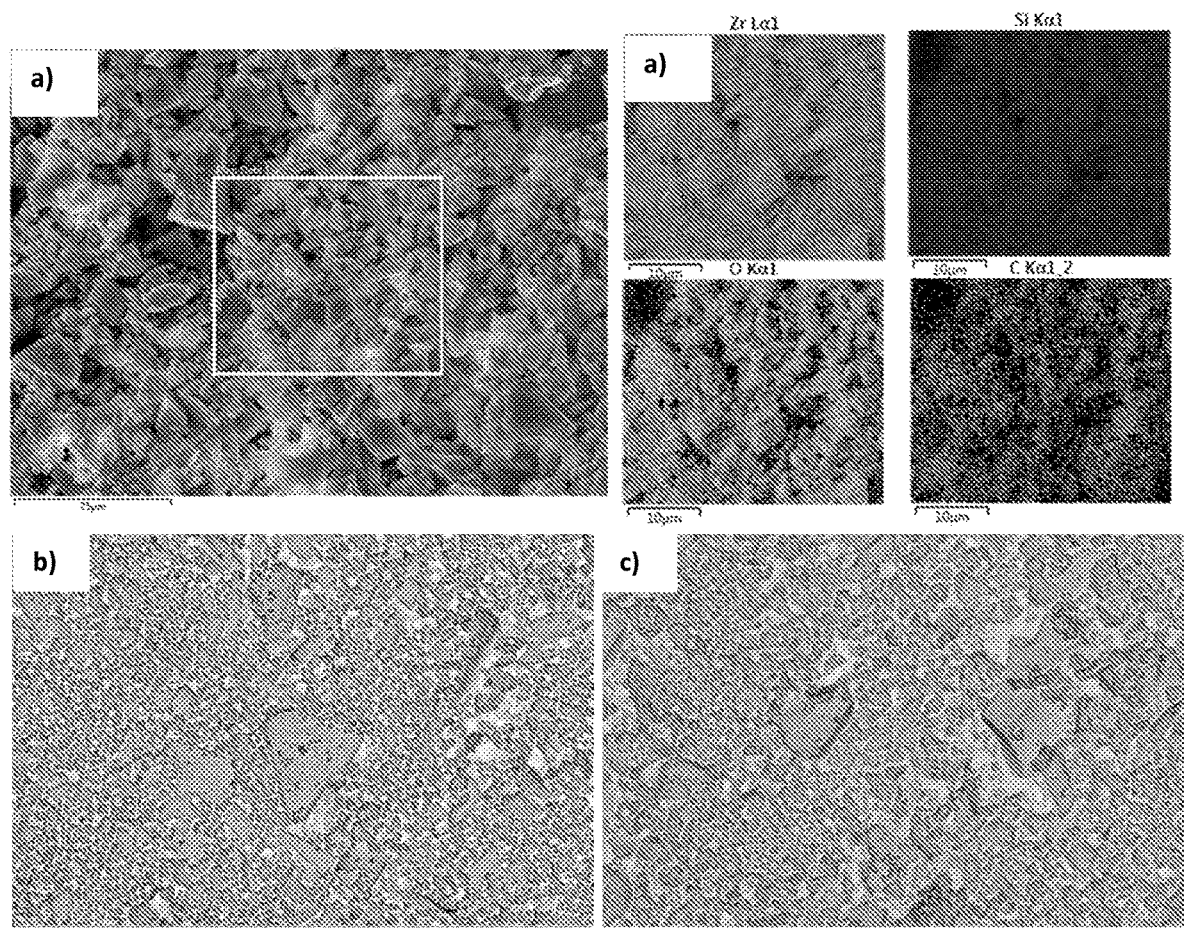
FIG. 4—SEM images of sol-gel powder after calcination. (a) 45Zr, EDS spectrums indicate that Zr, Si and O elements homogenously distribute in both crystal-like particles and small fragments; (b) 55Zr; (c) 65Zr.

XRD was used to investigate the degree of crystallinity of the pre-calcined powders. Results (FIG. 2a) showed that raw sol-gel powders of the three different compositions were all amorphous before calcination. Different crystallization behaviors occur with different compositions. 45Zr powder remained amorphous after calcination at 600° C. for 1 h, while 55Zr and 65Zr powders showed a weak peak around 30° which correspond to the highest peak of tetragonal ZrO$_2$ (FIG. 2b). It means that small amount of tetragonal ZrO$_2$ crystallize from the amorphous raw so-gel powder during calcination. The calcined 65Zr powder was observed with high resolution TEM. The power was mainly composed of amorphous phase, as indicated in FIG. 3a, while there are regions where clear lattice fringes can be observed and diffraction spots appeared in the inserted faster Fourier transform (FFT) patterns see FIG. 3b. The d-spacings, calculated from the lattice fringes (3.07 Å and 2.97 Å) is comparable to the reported (111) d-spacing of tetragonal ZrO$_2$ (2.964 nm). Together with XRD results, it can be concluded that the observed nano-sized crystals (approximately 5 nm) are tetragonal ZrO$_2$ nanocrystals. SEM observation (FIG. 4) of the powders showed that they shared similar morphology, consisting of relatively large particles (4-10 μm) and small irregular particles (less than 1 μm). EDS mapping (FIG. 4) of 45Zr powder indicated that Zr, Si and O elements homogenously distribute in both large particles and small irregular particles.

Characterization of the ZrO$_2$—SiO$_2$ Glass Ceramic Composition and Density

Figure 5:
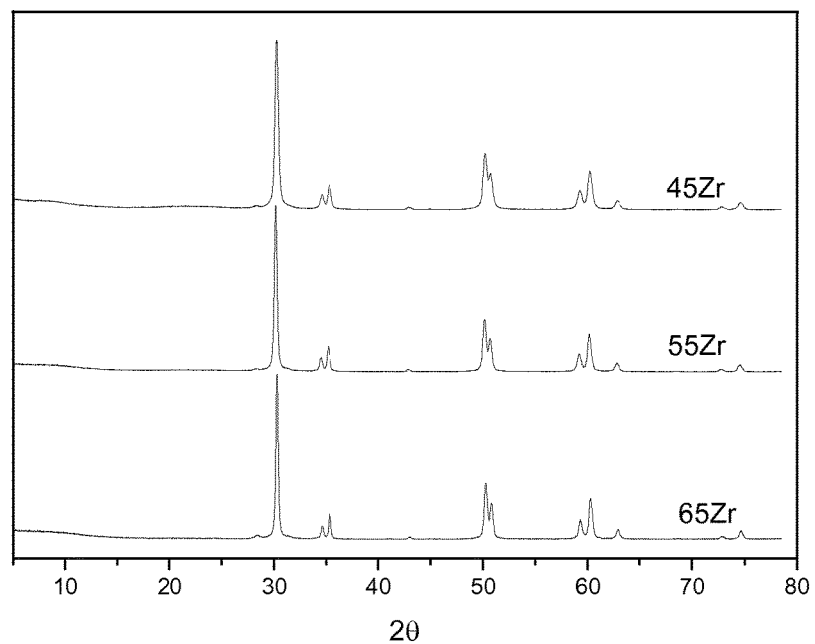
FIG. 5—XRD patterns of samples sintered under 1150-5-60, revealing that the crystal phase in all samples was tetragonal $ZrO_2$. No obvious peaks of $SiO_2$ and monoclinic $ZrO_2$ were found.

To confirm that the content of ZrO$_2$ and SiO$_2$ in SPSed glass ceramic samples matches our design compositions, the SPSed samples were analyzed with XRF. The results are listed in Table. 3 and the real composition of obtained ceramic specimens matched the nominal compositions well. XRD results (FIG. 5) showed that the sintered glass ceramics with the three different compositions were merely composed of tetragonal $ZrO_2$ and $SiO_2$ remained amorphous. The apparent density of 45Zr, 55Zr and 65Zr glass ceramics were 3.82 g/cm$^3$, 4.14 g/cm$^3$ and 4.53 g/cm$^3$, respectively. The density increases with the increase of $ZrO_2$ content, which is understandable since $ZrO_2$ is heavier than $SiO_2$. All glass ceramics achieved full densification (≥97% of theoretical density), see Table. 2.

TABLE 3

Nominal molar ratio, nominal mass ratio, mass ratio measured by XRF and volume fraction of $ZrO_2$—$SiO_2$ glass ceramics.

| Material | Nominal molar ratio | Nominal mass ratio | Mass ratio measured by XRF | Volume fraction |
|---|---|---|---|---|
| 45Zr | 45%Zr—55%Si | 62.6%Zr—37.4%Si | 64.1%Zr—34.5%Si | 39.7%Zr—60.3%Si |
| 55Zr | 55%Zr—45%Si | 71.5%Zr—28.5%Si | 71.1%Zr—27.6%Si | 47.7%Zr—52.3%Si |
| 65Zr | 65%Zr—35%Si | 79.2%Zr—20.8%Si | 78.1%Zr—19.5%Si | 58.7%Zr—41.3%Si |

Note:
Volume is calculated by mass divided by density. Volume fraction = V ($ZrO_2$ or $SiO_2$)/V ($ZrO_2$ + $SiO_2$). Zr represents $ZrO_2$, Si represents $SiO_2$.

Fracture Surface and Etched Sample Surface Morphology

Figure 6:
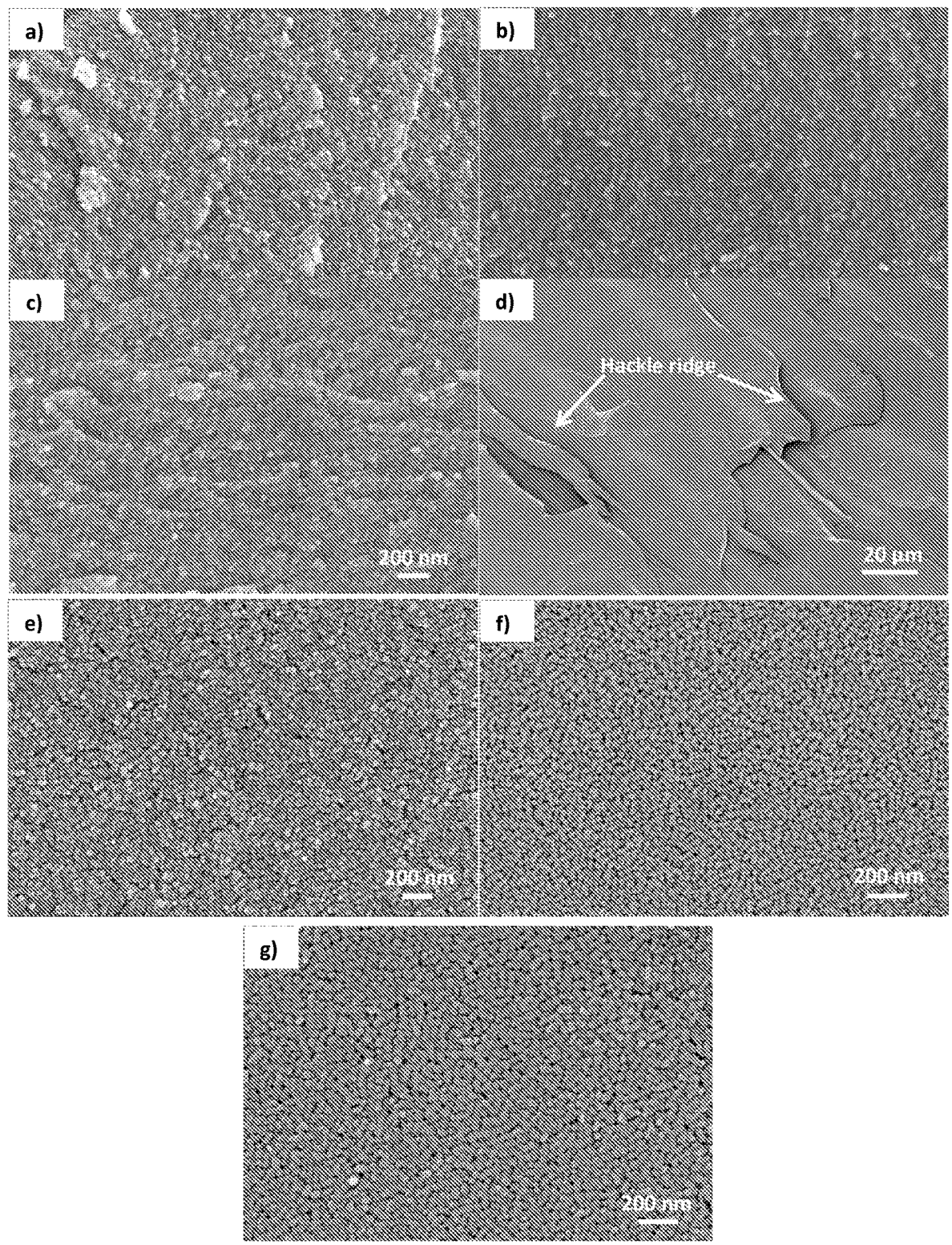
FIG. 6—SEM images of fracture surface after bending test: (a) 45Zr; (b) 55Zr; (c-d) 65Zr, and sample surfaces after HF gel etching for 1h: (e) 45Zr; (f) 55Zr; (g) 65Zr.

The fracture surface of the glass ceramics were examined with SEM after piston-on-three ball bending test. Large amount of nano-sized $ZrO_2$ particles and holes can be found on the fracture surface of the three ceramics. Judging that the particles and holes are in the same size level, we tend to think that nano-sized $ZrO_2$ particles were pulled out during bending test, leaving corresponding holes (FIGS. 6a, b and c). With careful observation of the three images, it can be found that the majority of $ZrO_2$ particles in 45Zr sample were isolated, while particles in 65Zr sample contacted and connected with each other. This is due to the fact that in 45Zr sample amorphous $SiO_2$ was matrix, accounting for 60.3% (volume fraction, Table. 2), and $ZrO_2$ particles acted as a second phase, imbedded in matrix (39.7%). On the contrary, in 65Zr sample the matrix phase was $ZrO_2$ (58.7%), building the three dimensional framework of the sample, and the rest 41.3% amorphous $SiO_2$ filled the space of the $ZrO_2$ framework. Therefore, $ZrO_2$ particles in 45Zr sample looked more isolated than those in 65Zr sample. The three glass ceramics exhibited a typical brittle conchoidal fracture behavior during the bending test, indicated by the fracture-surface morphology (FIG. 6d, images of 45Zr and 55Zr samples were not shown). SEM images of etched sample surfaces (FIG. 6e, f, g) offered an overview of size and morphology of $ZrO_2$ particles. All of the three ceramics presented homogenous $ZrO_2$ particles size distribution, without abnormal growth. It can be found that particle size in 65Zr sample was relatively larger than that of 45Zr and 55Zr samples. This is in agreement with crystal size values measured by XRD (Table. 2), 29.5 nm, 35.1 nm and 47.5 nm, for 45Zr, 55Zr and 65Zr, respectively.

Translucency

Figure 7:
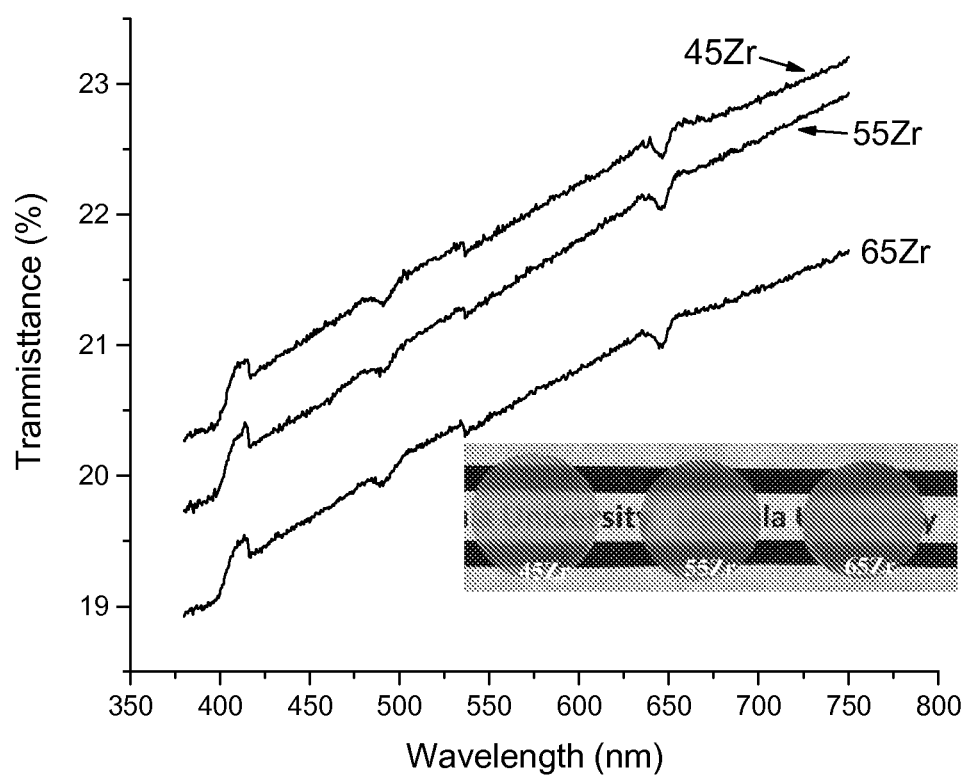
FIG. 7—Optical images of SPSed glass ceramic, with a thickness of approximately 1 mm.

As can be seen from FIG. 7, the SPSed samples presented high translucency, achieving approximately 20% transmittance. The text under 45Zr sample can be clearly recognized, while that under 65Zr sample was blurry, hard to recognize. But the stripes under 65Zr sample can easily be distinguished.

Microstructure of 65Zr Sample Characterized by TEM

Figure 8:
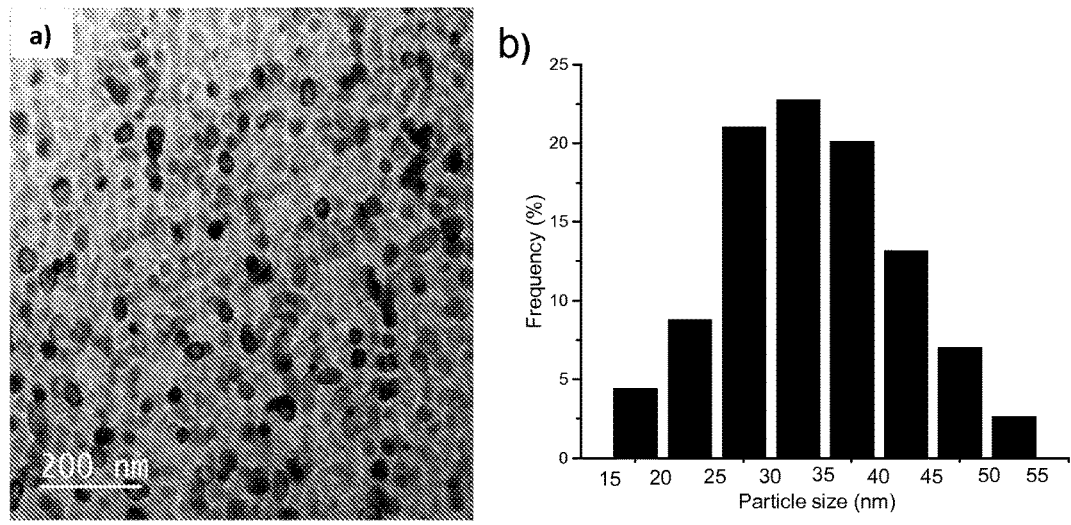
FIG. 8—Bright-field TEM image of 65Zr sample (a), and $ZrO_2$ particle size distribution measured from BF image (b).
Figure 9:
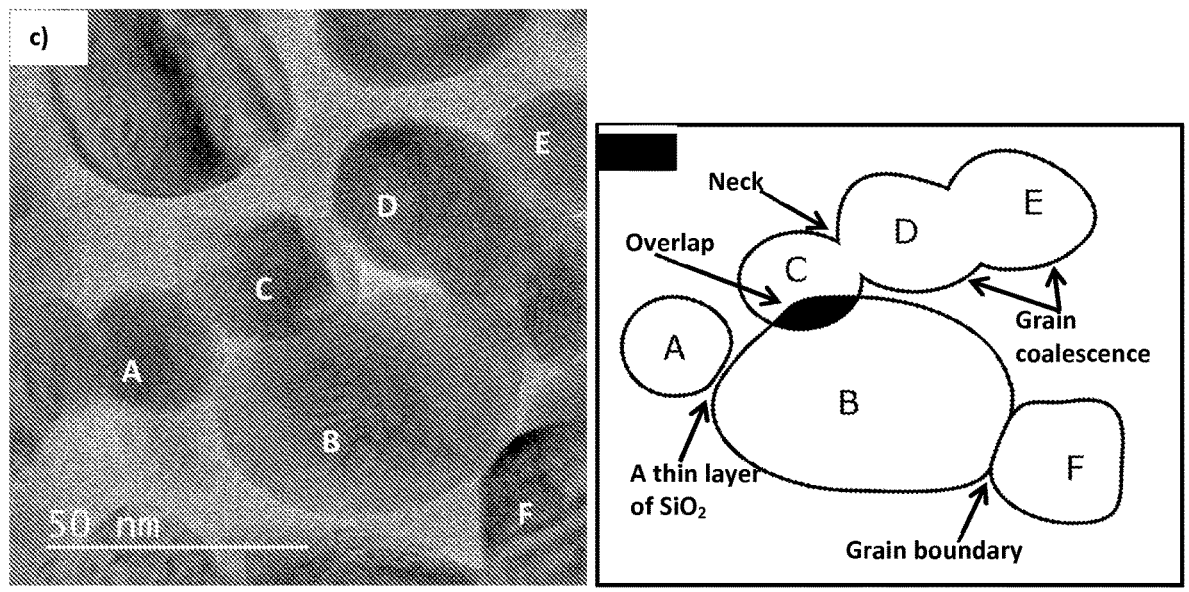
FIG. 9—HRTEM results of 65Zr sample, (a) $ZrO_2$ particles with different sizes embedded in $SiO_2$ matrix; (b) schematic of the relation between neighboring $ZrO_2$ particles, the capital letters correspond to those in figure (a).
Figure 10:
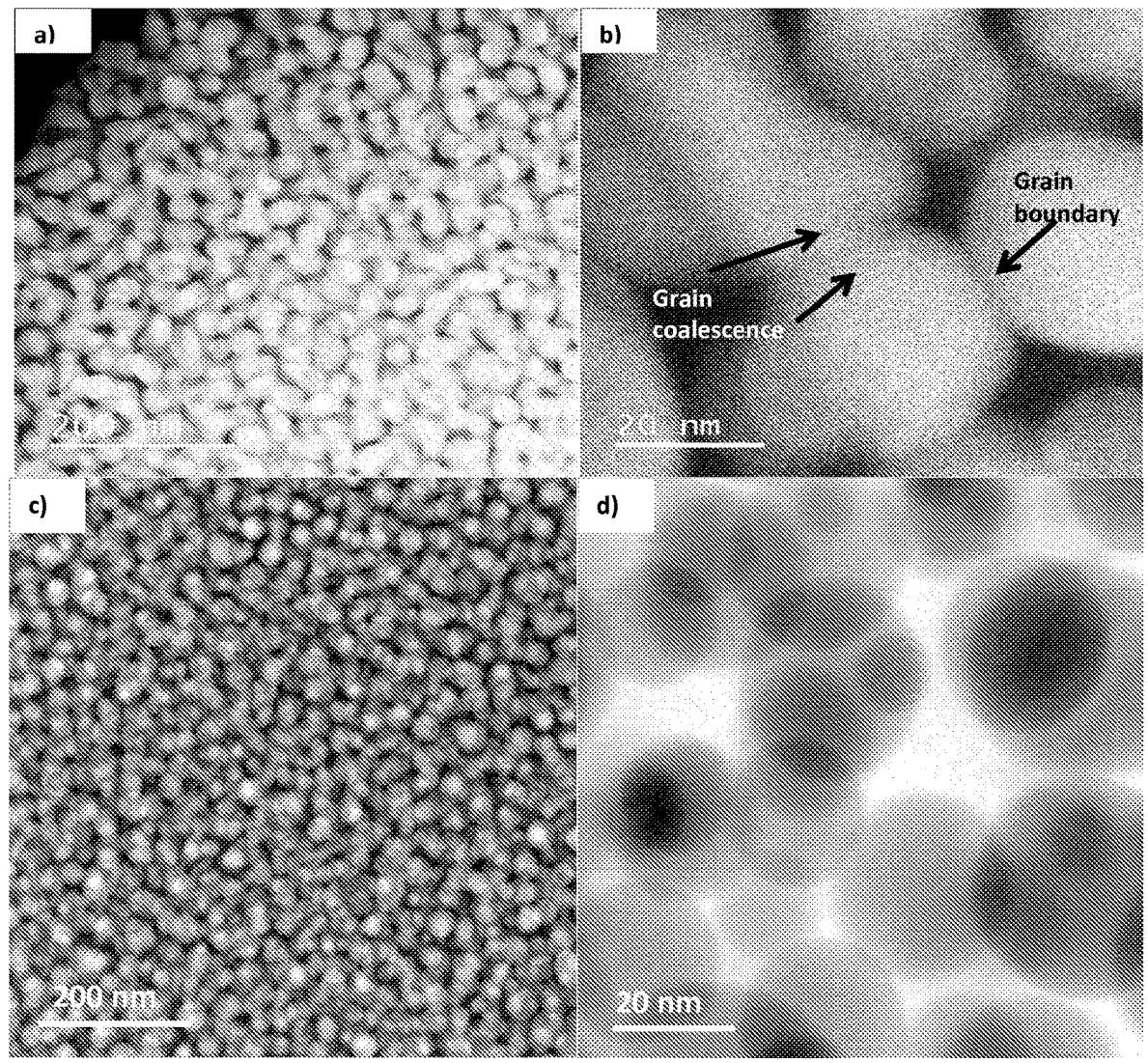
FIG. 10—HAADF STEM images of nano-sized $ZrO_2$ particles, (a), (b) 65Zr sample at low and high resolution, respectively; (c),(d) 35Zr sample as reference. $ZrO_2$ particles in 35Zr sample were almost perfectly spherical and isolated without much contact, while particles in 65Zr sample were elliptic with grain boundary and coalescence.
Figure 11:
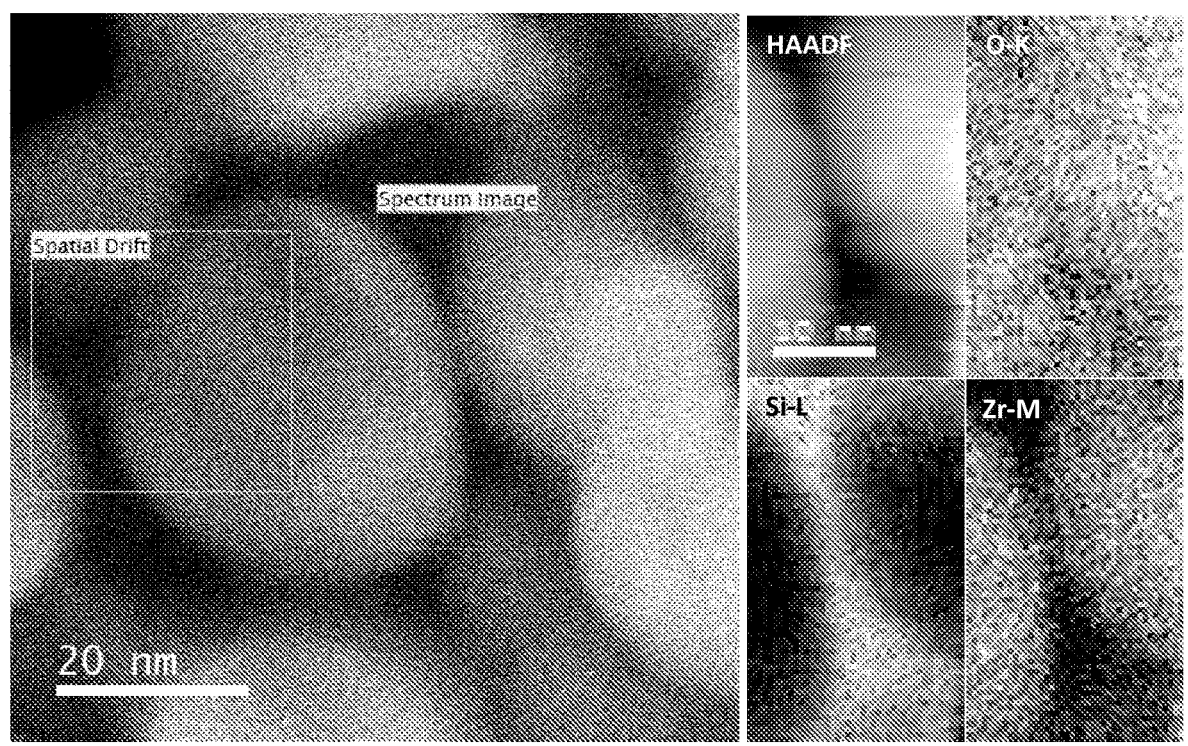
FIG. 11—EELS mapping of 65Zr sample indicates elemental distribution of O, Si and Zr. There is a thin layer of $SiO_2$ between the two $ZrO_2$ particles.

A typical bright-field TEM image (FIG. 8a) showed that the majority of $ZrO_2$ particles had an ellipsoidal morphology. Particle size distribution measured from FIG. 8a using a software indicated a Gaussian distribution of $ZrO_2$ ellipsoid with size ranging from 15.2 nm to 56.8 nm and a mean value of 34.8 nm (FIG. 8b). As can be clearly seen from HRTEM image (FIG. 9a), there were large $ZrO_2$ particles (particle B) and relatively smaller particles (particle A and E). The arrangement of $ZrO_2$ particles are of great interest. FIG. 9b revealed a schematic of the relation between neighboring $ZrO_2$ particles. The capital letters in FIG. 9b correspond to those in FIG. 9a. There was a thin layer of $SiO_2$ between particle A and B. Particle C and particle B located in different heights in the TEM specimen, resulting in an overlap in the image. A neck region can be observed between particle C and D, while grain coalescence was occurring between particle D and E, indicating the occurrence of grain growth process in the late stage of SPS. The authors tend to believe that the elliptic $ZrO_2$ particles in FIG. 8a are the result of grain coalescence. $ZrO_2$ particles with ellipse-like morphology can be clearly observed via the high-annular dark field scanning TEM (HADDF-STEM) images (FIG. 10a) which provides phase contrast. STEM images at higher magnification (FIG. 10b) demonstrated both grain boundary and coalescence. To demonstrate the microstructure evolution of the glass ceramic with the increase of $ZrO_2$ content, two STEM images of 35Zr sample were used for comparison in the FIG. 10. As can be seen from FIGS. 10c and d, the $ZrO_2$ particles were almost perfectly spherical without noticeable contact, while $ZrO_2$ particles in 65Zr sample were elliptical with grain boundary and coalescence which could be due to grain growth during SPS process. Another difference is 65Zr sample was compactly filled with $ZrO_2$ particles without much space ($SiO_2$ matrix), while $ZrO_2$ crystals in 35Zr sample were loosely embedded and separated $SiO_2$ matrix. EELS spectrums (FIG. 11) revealed a distinct distribution of Zr and Si in particles and matrix, respectively. And O distributed homogenously in both particles and matrix. The two $ZrO_2$ particles were separated by a thin layer of $SiO_2$ with a thickness of approximately 3 nm.

Mechanical Properties

The sintered samples were carefully grinded and polished before mechanical property tests to minimize the negative effects of flaws and defects on sample surface. The surface roughness values reached nanometer-scale (Table. 2). The mechanical properties were summarized in Table. 4. The overall trend is that all the listed mechanical properties increase with the increase of $ZrO_2$ content. The average value of 45Zr, 55Zr and 65Zr sample was 4.16 MPa$\sqrt{m}$, 5.58 MPa$\sqrt{m}$ and 6.83 MPa$\sqrt{m}$, respectively. The crack length emanating from indention also were 39.9 μm, 26.1 μm and 18.8 μm for 45Zr, 55Zr and 65Zr sample (Table. 2), respectively, also indicating that 65Zr sample has stronger resistance of crack propagation. In present study, the improvement of toughness was mainly attributed to the increase of $ZrO_2$ content which leading to stronger transformation effect. From another point view, a higher Young's modulus value leads to a higher mechanical strength (Eq. 2). The Young's modulus increases when more $ZrO_2$ is added, as listed in Table. 4, thus result in higher toughness. The flexural strength of 45Zr, 55Zr and 65Zr sample was 757 MPa, 818 MPa and 1063 MPa, respectively.

TABLE 4

Mechanical properties of studied $ZrO_2$—$SiO_2$ glass ceramic (average values ± standard deviation)

| Material | Micro-hardness (GPa) | Nano-hardness (GPa) | Biaxial flexural strength (MPa) | Young's modulus (GPa) | Fracture (MPa√m) toughness |
|---|---|---|---|---|---|
| 45Zr | 7.33 ± 0.17 | 9.07 ± 0.62 | 757 ± 122 | 106.0 ± 2.9 | 4.16 ± 0.53 |
| 55Zr | 7.11 ± 0.08 | 9.78 ± 0.53 | 818 ± 196 | 126.4 ± 7.0 | 5.58 ± 0.33 |
| 65Zr | 7.57 ± 0.11 | 11.35 ± 0.47 | 1063 ± 165 | 143.9 ± 4.9 | 6.83 ± 0.35 |

Example 3

Hot Isostatic Sintering (HIP) to Obtain $ZrO_2$—$SiO_2$ Glass Ceramic

The pre-calcined sol-gel powders could also be sintered by means of hot isostatic sintering (HIP). Green bodies were shaped by cold isostatic pressing method. The disk shaped (diameter 20 mm, thickness 3.5 mm) was made by die pressing under 20 MPa, then isostatically cold pressed under 240 MPa for 3 min. The green bodies were presintered in a furnace in air at 1350° C. for 2 h with a ramping rate of 5° C./min.

Hot isostatic pressing was performed using the pre-sintered samples. The presintered samples were set in an alumina container covered with an alumina plate to avoid contamination. The samples were maintained for 1 h at 1650° C. under an argon gas pressure of 150 MPa. In this treatment, temperature and pressure were simultaneously elevated with a heating rate of 10° C./min.

Example 4

Hot Pressing (HP) to Obtain $ZrO_2$—$SiO_2$ Glass Ceramic

The pre-calcined sol-gel powders could also be sintered by means of hot pressing (HP). Green bodies were shaped by cold isostatic pressing method. The disk is shaped in diameter 25 mm and thickness 5 mm. The green bodies were pre-pressed by hand pressing (5 MPa). The samples were maintained for 3 h at 1200° C. with a load of 4 ton kg force (kgf). The ramping rate was 5° C./min.

The invention claimed is:

1. A method for manufacturing translucent $ZrO_2$—$SiO_2$ nanocrystalline glass ceramic, comprising the steps of:
   Providing a first solution by mixing a first precursor comprising silicon (IV), a solvent and an acidic aqueous solution, wherein the acidic aqueous solution has a concentration of 0.1-1 mol/L, whereby the first precursor is hydrolyzed;
   Providing a second solution by mixing a second precursor comprising zirconium (IV) and a solvent;
   Combining the first and second solutions, wherein the molar ratio between Zr and Si in said solution ranges from 20:80 to 90:10;
   Hydrolyzing the second precursor and polymerizing the combined solution by addition of an acidic aqueous solution having a concentration of 5-12 mol/L, to form a sol;
   Ageing the sol to form a clear sol;
   Polymerizing the clear sol by addition of an acidic aqueous solution;
   Ageing the clear sol to form a gel;
   Drying the gel to form a xerogel;
   Micronising of the xerogel to form a powder, and optionally including particle size selection;
   Calcining the powder, optionally with pre-compaction or compaction during the calcination process; and
   Sintering the calcined powder, optionally with pre-compaction or compaction during the calcination process.

2. The method according to claim 1, wherein said first precursor is selected from the group consisting of tetraethyl orthosilicate, ethyl silicate, and silicon alkoxides.

3. The method according to claim 1, wherein said second precursor is selected from the group consisting of zirconium alkoxide, such as zirconium(IV) propoxide or $Zr(OPr)_4$, zirconyl nitrate, $ZrOCl_2$ solution, and zirconium (IV) chloride.

4. The method according to claim 1, wherein the first solution solvent comprises anhydrous 1-propanol or anhydrous ethanol in a first precursor:solvent ratio of 1:1-1:3.

5. The method according to claim 1, wherein the second solution solvent comprises ethanol, methanol or isopropanol in a second precursor:solvent ratio of 1:0.4 to 1:3.

6. The method according to claim 1, wherein the acidic aqueous solution is selected from a solution of HCl, $H_2SO_4$, $HNO_3$, and $CH_3COOH$.

7. The method according to claim 1, wherein the ageing of the sol is performed 0.5 to 24 hours at 20-80° C.

8. The method according to claim 1, wherein the ageing of the clear sol is performed for 3 hours to 3 days at 40-80° C.

9. The method according to claim 1, wherein the drying of the gel is performed for 1-3 days at 80-150° C.

10. The method according to claim 1, wherein the step of micronisation is performed by milling or by grinding.

11. The method according to claim 1, wherein the micronisation step is followed by a particle selection step/sieving step where a fraction having a particle size of 50-100 µm is selected.

12. The method according to claim 1, wherein the calcination is performed at 400-700° C. for 30 min 180 min.

13. The method according to claim 1, wherein the powder is compacted with or without heating before calcination or is compacted during calcination.

14. The method according to claim 1, wherein the sintering is performed by spark plasma sintering at temperatures of 900-1250° C. for 4-12 minutes.

15. The method according to claim 1, wherein the sintering is performed by hot isostatic pressing/hot pressing at temperatures of 900-1400° C. for 30-300 minutes.

16. The method according to claim 1, wherein the powder is compacted with or without heating before sintering or is compacted during sintering.

17. The method according to claim 1, wherein the first and second solutions are combined with the molar ratio between Zr and Si in said solution ranging from 60:40 to 80:20.

18. The method according to claim 1, wherein the step of micronisation is performed by planetary ball milling.

19. A precursor powder material for forming translucent glass ceramic material, the precursor powder material comprising $SiO_2$ and 5-10 wt % of nanocrystalline tetragonal $ZrO_2$, wherein the molar ratio between $ZrO_2$ and $SiO_2$ ranges from 60:40 to 80:20.

20. The precursor powder material according to claim 19, wherein the nanocrystalline tetragonal $ZrO_2$ is spherical with a crystal size that ranges from 10 nm to 50 nm.

21. A translucent glass ceramic material having a microstructure of single crystalline $ZrO_2$ spherical nanocrystals embedded in an amorphous $SiO_2$ matrix, wherein the molar ratio between $ZrO_2$ and $SiO_2$ ranges from 60:40 to 80:20 and the material comprises 5-10 wt % of the $ZrO_2$ spherical nanocrystals.

22. The material according to claim 21, wherein the crystal size of the $ZrO_2$ spherical nanocrystals ranges from 10 nm to 400 nm.

23. The material according to claim 21, wherein the only crystalline phase in the material is tetragonal $ZrO_2$.

24. The material according to claim 21, wherein at least 99% of the material is fully densified.

25. The material according to claim 21, wherein the flexural strength of the material is above 400 MPa and the fracture toughness is above about 2 $MPa^{\sqrt{m}}$.

26. The material according to claim 25, wherein the flexural strength of the material is above 600 MPa.

27. A dental restorative material comprising a translucent glass ceramic material having a microstructure of single crystalline $ZrO_2$ spherical nanocrystals embedded in an amorphous $SiO_2$ matrix, wherein the molar ratio between $ZrO_2$ and $SiO_2$ ranges from 60:40 to 80:20 and the material comprises 5-10 wt % of the $ZrO_2$ spherical nanocrystals.

* * * * *